United States Patent
Bartsch

(10) Patent No.: US 6,759,572 B2
(45) Date of Patent: Jul. 6, 2004

(54) PROCESS FOR PRODUCING FEMALE STERILE PLANTS

(75) Inventor: Klaus Bartsch, Königstein (DE)

(73) Assignee: Hoechst Schering Agrevo GmbH, Berlin (DE)

( * ) Notice: Subject to any disclaimer, the term of this patent is extended or adjusted under 35 U.S.C. 154(b) by 0 days.

(21) Appl. No.: 09/147,993

(22) PCT Filed: Sep. 15, 1997

(86) PCT No.: PCT/EP97/05037

§ 371 (c)(1),
(2), (4) Date: Mar. 24, 1999

(87) PCT Pub. No.: WO98/13504

PCT Pub. Date: Apr. 2, 1998

(65) Prior Publication Data

US 2002/0002710 A1 Jan. 3, 2002

(30) Foreign Application Priority Data

Sep. 26, 1996 (DE) .......................... 196 39 463

(51) Int. Cl.⁷ ......................... C12N 15/05; C12N 15/31; C12N 15/82; A01H 5/00; A01H 1/02
(52) U.S. Cl. ....................... 800/287; 800/278; 800/300; 800/303; 800/288; 800/271; 435/69.1; 536/23.2; 536/23.7; 536/24.1
(58) Field of Search ................................. 800/287, 300, 800/288, 278, 290, 303, 271; 435/69.1; 536/23.2, 23.7, 24.1

(56) References Cited

U.S. PATENT DOCUMENTS

| 5,650,310 A | 7/1997 | Broer et al. | ............. | 435/172.3 |
| 5,668,297 A | 9/1997 | Broer et al. | ................ | 800/205 |

FOREIGN PATENT DOCUMENTS

| DE | 41 26 414 A1 | 2/1993 | | |
| DE | 43 08 061 A1 | 9/1994 | | |
| EP | 0 412 006 A1 | 2/1991 | | |
| WO | WO 94/25613 | 11/1994 | ................ | 800/287 |
| WO | WO98/39462 | * 9/1998 | | |

OTHER PUBLICATIONS

Turget et al. Plant Molecular Biology 24: 97–104, 1994.*
Thorsness et al. Developmental Biology 143, 173–184, 1991.*
Kriete et al., The Plant Journal, 1996, vol. 9, No. 6, pp. 809–818.
Crabeel et al. (1977) "Studies on the Bipolar *argECBH* Operon of *E. coli*: Characterization of Restriction Endonuclease Fragments Obtained from λ*dargECBH* Transducing Phages and a ColE1 *arg ECBH* Plasmid" Molec. Gen. Genet. 151:161–168.
Crabeel et al. (1979) "Cloning and Endonuclease Restriction Analysis of *argF* and of the Control Region of the *argECBH* Bipolar Operon In *Escherichia coli*" Gene 5:207–231.
Piette et al. (1982) "The Regulatory Region of the Divergent *argECBH* Operon in *Escherichia coli* K–12" Nucl. Acids Res. 10: 8031–8044.
Meinnel (1992) "Structural and Biochemical Characterization of the *Escherichia coli argE* Gene Product" J. Bact. 174:2323–2331.
Boyen, et al. (1992) "Acetylornithine deacetylase, succinyl-diaminopimelate desuccinylase and carboxypeptidase G2 are evolutionarily related" Gene 116:1–6.
Dzelzkalns VA, Thorsness MK, Dwyer KG, Baxter JS, Balent MA, Nasrallah ME, Nasrallah JB. Distinct cis–acting elements direct pistil–specific and pollen–specific activity of the Brassica S locus glycoprotein gene promoter. Plant Cell. 1993 Aug.; 5(8): 855–63.
Robert et al. Molecular analysis of two Brassica napus genes expressed in the stigma. Plant Mol Biol. 1994 Nov.; 26(4): 1217–22.

* cited by examiner

*Primary Examiner*—David T. Fox
*Assistant Examiner*—Medina A. Ibrahim
(74) *Attorney, Agent, or Firm*—Frommer Lawrence & Haug LLP

(57) ABSTRACT

The invention relates to processes for producing transgenic plants using tissue-specific promoters. In these plants, the development of particular plant parts can be prevented deliberately.

6 Claims, No Drawings

SEQUENCE LISTING

<160> NUMBER OF SEQ ID NOS: 4

<210> SEQ ID NO 1
<211> LENGTH: 289
<212> TYPE: DNA
<213> ORGANISM: Brassica oleracea

<400> SEQUENCE: 1
attttctaac agacttagat gcacttgcga acaacatact tgctgaacac catatgttat    60

-continued

```
gttggcaggg tgagaaatta atcacgtgta gatatagaag tagtagacaa atgatatagg      120
tttgtgggaa tgaattaatc gatgggatga aaaagtcatc gaacatgtaa caccacattt      180
tacttgtctg ctaggttcgt gatagtcgtt taaattagat acgtgaaaaa agattataaa      240
atatgcaaaa ggggaagggg aagaaagaaa gaaaaaggag gggagagaa                 289

<210> SEQ ID NO 2
<211> LENGTH: 312
<212> TYPE: DNA
<213> ORGANISM: Brassica oleracea

<400> SEQUENCE: 2
acttgaatgt atcgaatcat actattgaga ccaccatact tgcggaatac catatgctat       60
gttgacagcg tgagaactaa taacgtgtag atataaaagt agttgactga atgatacaag      120
tttgtggaag tgacttaatc gtagggatga aaaagtcatg gactatggaa cacaacattt      180
tgcttgccag ttaggttcgt cataagtcgt ttaaattaga tacgtgaaaa agataactta      240
ggatgtatat atatgtgcaa gtaggacaaa aactaacaac aagaaaaaaa aagaaagaaa      300
gtggtgggga aa                                                         312

<210> SEQ ID NO 3
<211> LENGTH: 202
<212> TYPE: DNA
<213> ORGANISM: Brassica campestris

<400> SEQUENCE: 3
gtagtaggta taaaagtagt ggacaaatga tacacgtttt tggaaatgaa ttaatcgatg       60
ggatgaaaaa gtcatcgaac atgtaacacc acattttgct tgtctgctag gttccttata      120
gtcgtttaaa atctgtatgt ggaaaagatt ataaataagc aagggagggg ggaaagaaag      180
aaagaacaag gtggggagag aa                                              202

<210> SEQ ID NO 4
<211> LENGTH: 356
<212> TYPE: DNA
<213> ORGANISM: Brassica oleracea

<400> SEQUENCE: 4
ttttaagtca aactgaagga aacaacatat gatatgttat gtcatttggt ccaaaaacac       60
aatgttacgt tgcatgagaa atcaatttca cgtggtaagg ttactgacca atgacaatag      120
tttgttaaaa tgagttaatg tagggatgga aagtcataga atgtggaaat aaaaaatttt      180
cttgtctgct ggaaagtata taatatctac aattaagaca taaaccatgc aaattaaaat      240
caaaccatcc tcattaggtt tgcaaatcta ataaagaata aaagtccata tgtaacaatt      300
tttttctata aataacgggc gacaatgcat agaaaattaa agtggtgaag agagag          356
```

PROCESS FOR PRODUCING FEMALE STERILE PLANTS

CROSS-REFERENCE TO RELATED APPLICATIONS

This application corresponds to PCT/EP/97/05037 filed Sep. 15, 1997, designating the U.S., which claims priority from German Patent Application 196 39 463.5 filed Sep. 26, 1996. Each of these documents are incorporated herein by reference.

The invention relates to the use of deacetylase genes for producing transgenic plants while employing tissue-specific promoters. In these plants, the development of particular plant parts can be prevented deliberately.

BACKGROUND OF THE INVENTION

Phosphinothricin (PTC, 2-amino-4-methylphosphinobutyric acid) is an inhibitor of glutamine synthetase (GS). PTC is a "building block" of the antibiotic phosphinothricylalanylalanine. This tripeptide (PTT) is active against Gram-positive and Gram-negative bacteria and also against the fungus Botrytis cinerea. PTT is produced by the Streptomyces viridochromogenes strain Tü494, which is deposited in the Deutsche Sammlung für Mikroorganismen (German collection of microorganisms) under numbers DSM 40736 and DSM 4112 and which is obtainable from this source. It is known from German patent specification 2 717 440 that PTC acts as a total herbicide. The published application (EP-A-0257542) (corresponding to U.S. Pat. No. 5,273,894) describes how a phosphinothricin N-acetyltransferase (pat) gene can be used to produce herbicide-resistant plants. The phosphinothricin N-acetyltransferase which is encoded by the pat gene modifies the PTC which appears intracellularly and detoxifies the herbicide.

DESCRIPTION OF THE INVENTION

The present invention now describes the use of deacetylase genes (dea), whose expression products are able to deacetylate N-acetylphosphinothricin (N-Ac-PTC) and/or N-Ac-PTT intracellularly, and thereby restore their antibiotic activity, for producing female-sterile plants.

An N-acetylphosphinothricin tripeptide deacetylase gene can be isolated from S. viridochromogenes Tü494. The dea gene is located downstream of the pat gene on the already known 4.0 kb BamHI fragment (EP-A-0 257 542) (corresponding to U.S. Pat. No. 5,273,894). This gene is located on a BglII/BamHI fragment and is fixed precisely by the sequence. The protein sequence is defined by the DNA sequence.

An ATG codon, which is recognized in bacteria and plants, is used as the translation start codon. This gene encodes the last step in the biosynthesis of PTT, i.e. the deacetylation of inactive N-acetylphosphinothricin tripeptide to give the active PTT.

It is known that the specificity of many enzymes is not restricted to one substrate. Thus, the phosphinothricin N-acetyltransferase which is encoded by the pat gene is actually used in PTT biosynthesis for acetylating desmethyl-PTC and, because of its lack of specificity, can be used for detoxifying PTC. By means of overexpressing the dea gene (using suitable promoters or by cloning onto high-copy vectors), an insufficiently specific N-acetyl-PTT deacetylase can now be employed for activating N-acetylphosphinothricin.

Other dea genes can be isolated from E. coli. Thus, it has been found that in E. coli, in contrast to other bacteria (e.g. rhizobias and streptomycetes), no activity can be detected in the so-called pat assay (dissertation of Inge Broer, University of Bielefeld Faculty of Biology, Expression des Phosphinthricin-N-Acetyltransferase-Gens aus Streptomyces viridochromogenes in Nicotiana tabacum (Expression of the Streptomyces viridochromogenes phosphinothricin N-acetyltransferase gene in Nicotiana tabacum), pp. 42–43, 1989) after the pat gene has been cloned into suitable expression vectors (Strauch et al., Gene, 63, 65–74, 1988; Wohlleben et al., Gene, 70, 25–37, 1988). In addition, when present in low copy number in E. coli, the pat gene is unable to confer resistance to PTT since the endogenous deacetylase nullifies the effect of the phosphinothricin N-acetyltransferase. Finally, this deacetylase activity can be demonstrated directly by the efficient inhibition of GS activity which occurs after adding N-acetylphosphinothricin. The deacetylase converts N-Ac-PTC into PTC, which then inhibits the GS in a known manner, as can be measured in a γ-glutamyltransferase assay (Bender et al., J. Bacteriol. 129, 1001–1009, 1977). This is due to the possession by E. coli of an endogenous deacetylase activity.

This activity is apparently not present in the argE mutant which is known from the literature (Baumberg, Molec. Gen. Genetics 106, 162–173, 1970). Other E. coli deacetylase mutants are easy to select: following classical (Delić et al., Mut. Res. 9, 167–182, 1970; Drake and Baltz, Ann. Rev. Biochem. 45, 11–38, 1976) or Tn5 mutagenesis (Kleckner, Ann. Rev. Genet. 15, 341–404, 1981), such mutants can be recognized on PTT-supplemented minimal medium by the fact that it is only they which are able to grow after having been transformed with a pat gene which is cloned into a low copy number vector.

The E. coli deacetylase gene can therefore be isolated by using conventional methods (Maniatis et al., Molecular Cloning: a Laboratory Manual, Cold Spring Harbor Laboratory, Cold Spring Harbor, N.Y., 1982) to construct a gene library in, for example, the E. coli argE mutant or in a freshly isolated mutant.

Methods for isolating other deacetylase genes can be inferred from that which is described above: e.g. isolating new organisms which are PTT-sensitive despite the presence of a pat gene on a low copy number vector, and subsequently isolating a deacetylase gene.

In a further aspect of the invention, pat and dea genes can be employed together with tissue-specific promoters for deliberately preventing the development of particular plant tissues. An example of a special application is that of producing female-sterile plants.

In plant breeding, the production of hybrid seed depends on avoiding self-fertilization of the parent plant with a high degree of certainty. Male-sterile mutants, which are employed in breeding, occur naturally in many plant species. The molecular mechanism of cytoplasmic male sterility (cms) has not so far been completely clarified. In addition, many crop varieties, such as Beta vulgaris, do not have any cms variant. It is therefore of great interest to agriculture to use the genetic engineering route to generate defined sterile mutants of all the important crop varieties. The company PGS/Belgium has presented such a method in patent application PCT/EP 89/00495. This method is based on destroying the tissue (tapetum) surrounding the pollen parent cells. For this purpose, an RNAse gene is fused to a tapetum-specific promoter (Mariani et al., Nature 347, 737–741, 1990). The exclusive expression of the gene in the tapetum cells ensures that the tissue is destroyed selectively and thereby prevents the mature pollen from being formed. According to this patent, a plant which carries this gene is only able to form seeds following allogamy.

An important disadvantage of this system is the fact that the progeny of this plant are likewise male-sterile and are therefore unable to form any seeds in the field, where they have to rely on self-fertilization. Success in forming seeds is only achieved if the male partner of the cross carries a gene which is able to neutralize the effect of the RNAse in the progeny. According to the abovementioned laid-open patent application, this is supposed to be effected by the barstar gene. In fact, it is only genetically modified, i.e. transgenic partners which can be used in the cross in this context.

Processes for producing female-sterile plants (fs plants), which processes allow transgenic parent plants to be crossed with any partners of the same species, are presented below. This is achieved by the combination of a dea gene under the control of a promoter which is selectively active in the female organs, where appropriate in combination with a constitutively expressed pat gene. The glutamine synthetase in the cells is specifically inhibited, and these cells are caused to die, by applying PTC and/or PTT. An even simpler system comprises producing transgenic plants which only contain one single foreign gene, namely a dea gene under the control of a tissue-specific, in this case female-specific promoter, and then applying N-Ac-PTC and/or N-Ac-PTT to the plant.

To generalize, the invention consequently comprises tissue-specific inhibition with the aid of a deacetylase gene.

1) Plants which are resistant to PTT and/or PTC as a result of Pat activity (e.g. produced as described in EP 0257542 (corresponding to U.S. Pat. No. 5,273,894) or EP 0 242 236) are transformed with a deacetylase gene under the control of the promoter which exhibits tissue-specific activity in plants. Following application of PTT or PTC, expression of the deacetylase gene leads to the activity of phosphinothricin N-acetyltransferase being neutralized in the corresponding tissues. These tissues are then killed selectively whereas the remainder of the plant is resistant.

This system can be simplified by using N-acetylphosphinothricin or N-acetylphosphinothricin-tripeptide. While neither substance is herbicidally active, they are both taken up by plants and transported and not degraded immediately. No deacetylation activity for N-acetylphosphinothricin and N-acetylphosphinothricin-tripeptide has so far been demonstrated in plants. In this way, the above-described 2-gene system can be reduced to a 1-gene system and thereby crucially simplified, as explained in more detail below: any plant can be transformed with a Streptomycetes-derived deacetylase gene under the control of a tissue-specific promoter. Following application of N-acetylphosphinothricin or N-acetylphosphinothricin-tripeptide, the tissue-specific expression leads to the immediate death of the corresponding tissue.

All the described promoters which have been demonstrated to elicit selective expression in particular tissues, preferably the female organs, can be used as tissue-specific promoters. In this connection, the term female organs encompasses the gametophyte and the tissue which surrounds or adjoins it, for example gynoecium (carpels), ovules, placenta, pistil (ovary, style and stigma).

Thus, Robert et al., for example, describe rape-derived stigma-specific promoters (Robert et al., 1994). Pistil-specific promoters have also been described (Sato et al., 1991; Dzelzkalns et al., 1993, WO 94/25613) (corresponding to U.S. Pat. No. 5,859,328).

However, promoters which, while not being specifically active in the female organs, are nevertheless expressed in a tissue which is essential for the development of the functional flower, embryo and seed, are also suitable for use in the process according to the invention.

All newly isolated promoters having similar properties are, of course, also suitable. Apart from tissue-specific promoters, those promoters which are subject to another type of regulation (e.g. temporal, stress-determined or environment-dependent) and which behave in a tissue-specific manner can also be employed.

These processes furthermore make it possible to analyze the differentiation of cell regulation and to produce plants in which the development of particular plant parts has been deliberately prevented. The process can preferably be employed for producing female-sterile plants.

EXAMPLES

Example 1

Fusing the Deacetylase-Encoding Region to Eukaryotic Transcription Signals

The plasmid pPRI (see EP-0 257 542) (corresponding to U.S. Pat. No. 5,273,894) was isolated from an *E. coli* strain and cleaved with BamHI and BglII. The digested DNA was fractionated in an agarose gel, and an 0.9 kb fragment was isolated from the gel. The vector pROKI (Baulcombe et al., Nature 321, 446–449, 1986) was likewise restricted with BamHI. The two mixtures were combined and ligated. The ligation mixture was transformed into *E. coli* S17.1 (Simon et al., Bio/Technology 1, 784–791, 1983). Colonies which grew on kanamycin-containing media were transferred to nitrocellulose filters and lysed after being incubated at 37° C. for 12 h. The bacterial DNA was fixed to the filter. The 0.9 kb fragment which was isolated from the agarose gel was rendered single-stranded by incubation at 100° C. The missing strand was then synthesized using Klenow polymerase and digoxigenin-labeled nucleotides. The labeled strand was used as the probe for hybridizing with the bacterial DNA which was bound to the filter. Hybridizing clones were detected by means of an antibody reaction. The DNA of the positive clones was isolated by means of Qiagen lysis and digested with BamHI/EcoRI and BamHI/HindIII. This restriction enables the orientation of the inserted 0.9 kb fragment to be determined. The plasmid having orientation I was designated pIB17.1, while that having orientation II was designated pIB17.2.

Example 2

Detecting the Deacetylation of N-acetyl-PTC and N-acetyl-PTT by the Deacetylase Gene It was possible to demonstrate that the eukaryotic transcription signals cloned in vector PROKI also permit expression in *R. meliloti*, *A. tumefaciens* and *E. coli*.

Plasmids pIB17.1 and pIB17.2 were therefore transferred by means of a 2 factor cross into the *Rhizobium meliloti* strain 2011. By incubating *R. meliloti* wild-type strains with radioactively labeled N-acetyl-PTC, it was possible to demonstrate that this strain does not deacetylate N-acetyl-PTC. (After incubating pIB17.1-harboring strains with N-acetyl-PTC and N-acetyl-PTT, the deacetylation can be demonstrated by means of thin layer chromatography). It was also possible to demonstrate that *R. meliloti* reacts very sensitively to PTC and PTT. The deacetylation can therefore also be demonstrated by means of the inhibition of the *R. meliloti* glutamine synthetases which is brought about by the liberated PTC.

Example 3

Transferring the Modified Deacetylase Gene into *Nicotiana tabacum*

The deacetylase gene which was modified in Example 1 was transferred into *A. tumefaciens* LBA4404 using a two-factor cross. *Nicotiana tabacum* leaf disks were incubated with the resulting strains LBA4404/17.1 and LBA4404/17.2 and, after 3 days, transferred to a kanamycin-containing shoot-inducing medium. Southern hybridization can be used to test regenerating kanamycin-resistant shoots for the presence of the deacetylase gene. Following treatment with N-acetyl-PTC or N-acetyl-PTT, the plants are then killed by the PTC or PTT, respectively, which is liberated.

Example 4

Constructing a Vector for Transiently Expressing the Modified Deacetylase Gene in *E. coli* and Tobacco Protoplasts The modified deacetylase gene from pIB17.1 and pIB17.2 was excised from the plasmids by means of EcoRI/HindIII digestion. The restricted DNA was fractionated in an agarose gel, and an 0.9 kb fragment was isolated in each case. The vector pSVB28 (Arnold and Pühler, Gene 70, 171–179, 1988) was likewise digested with EcoRI/HindIII. The two mixtures were combined and ligated. Following transformation into the β-galactosidase-negative *E. coli* strain JM83, all the vector-harboring clones exhibited a blue coloration whereas clones harboring a vector into which the deacetylase gene was inserted remained white. The DNA was isolated from the clones which had been identified in this way and digested with EcoRI/HindIII. It was possible to identify the clones containing the modified deacetylase gene on the basis of the restriction pattern. The vectors which were constructed have the designations pIB27.1 and pIB27.2. They are present in high copy number in *E. coli*.

Example 5

Transiently Expressing the Modified Deacetylase Gene into Tobacco Protoplasts The plasmic DNA was isolated from the *E. coli* strains constructed in Example 4. Young tobacco leaves were incubated with digestion enzymes for 20 h. The protoplasts precipitating from the leaf skeleton were purified and incubated in a transfer buffer containing polyethylene glycol (PEG) and the isolated DNA. The protoplasts were subsequently washed and resuspended in a culture fluid (K3 medium). After having been incubated for 3 days under dim illumination, the regenerating protoplasts were disrupted and the crude extracts were incubated with radioactively labeled N-acetyl-PTC and N-acetyl-PTT. The deacetylated PTC or PTT, respectively, can be detected by means of thin layer chromatography.

Example 6

Process for Producing Female-sterile Crop Plants Using the *S. viridochromogenes* Deacetylase Gene under the Control of a Pistil-Specific Promoter The *Streptomyces viridochromogenes* deacetylase gene is fused to a pistil-specific promoter and introduced into tobacco cells by way of agrobacterium-mediated leaf disk transformation. At an arbitrary time before flowering, the plants which regenerate from these cells are sprayed with N-acetyl-PTC or N-acetyl-PTT. It can be shown that N-acetyl-PTC is stable in the plant cell and transported into all cells. Neither of the two substances has recognizably negative consequences for the wild-type plant. As soon as the first pistil cells form, they begin to express the deacetylase gene. The N-acetyl-PTC or N-acetyl-PTT which is stored in the cell is deacetylated by the enzyme and thereby converted into its active form. It inhibits the glutamine synthetase of the cells and thereby leads to rapid death. Functional embryos or seeds can no longer be formed. Despite this, the development of the male organs of reproduction is not impaired. In addition, the formation of the deacetylase is also interrupted. Surrounding cells are not damaged. If the plant is not treated with N-acetyl-PTC or N-acetyl-PTT, it is completely fertile. It is not, therefore, necessary to neutralize the fs with a gene of the male partner of the cross. At the same time, the plant contains a precisely defined mutation which is without effect on its vigor and usefulness.

REFERENCES

Dzelzkalns et al., The Plant Cell, Vol. 5, 855–863, August 1993.
Robert et al., Plant Molecular Biology 26, 1217–1222, 1994.
Sato et al., The Plant Cell, Vol. 3, 867–876, September 1991.

---

I claim:

1. Process for producing transgenic plants containing selectively destructible plant parts, wherein an N-Ac-PTC or N-Ac-PTT deacetylase gene is placed under the control of a pistil- or stigma specific promoter, and the pistil- or stigma are caused to die by means of suitable, timely treatment with N-acetyl-PTC or N-acetyl-PTT.

2. Process according to claim 1, wherein the deacetylase genes derives from a soil microorganism and the plant is treated with N-acetyl-PTC or N-acetyl-PTT.

3. Process according to claim 1, whereby female-sterile plants are produced.

4. Female-sterile plants, or parts thereof, which can be prepared by a process according to claim 1.

5. The process according to claim 1, wherein the N-Ac-PTC or N-Ac-PTT deacetylase gene is from *Streptomyces viridochromogenes*.

6. The process according to claim 1, wherein the N-Ac-PTC or N-Ac-PTT deacetylase gene is from *E. coli*.

* * * * *